(12) United States Patent
Woolford et al.

(10) Patent No.: US 9,371,313 B2
(45) Date of Patent: Jun. 21, 2016

(54) PROCESS FOR EXTRACTING COMPOUND FROM CRANBERRY LEAVES AND RELATED PRODUCTS

(75) Inventors: Geoffrey Woolford, Lakeville-Middleboro, MA (US); Stanley Thompson Michalski, Lakeville-Middleboro, MA (US); Lawrence E. Rose, Lakeville-Middleboro, MA (US); Christina Khoo, Lakeville-Middleboro, MA (US); Rodney Arthur Serres, Lakeville-Middleboro, MA (US); Stephen Joseph Nojeim, Lakeville-Middleboro, MA (US); Martin Foster Berry, Lakeville-Middleboro, MA (US); Caroline Hennigar Vogel, Lakeville-Middleboro, MA (US)

(73) Assignee: Ocean Spray Cranberries, Inc., Lakeville-Middleboro, MA (US)

( * ) Notice: Subject to any disclaimer, the term of this patent is extended or adjusted under 35 U.S.C. 154(b) by 691 days.

(21) Appl. No.: 13/521,985

(22) PCT Filed: Jan. 14, 2011

(86) PCT No.: PCT/US2011/021431
§ 371 (c)(1), (2), (4) Date: Dec. 20, 2012

(87) PCT Pub. No.: WO2011/088420
PCT Pub. Date: Jul. 21, 2011

(65) Prior Publication Data
US 2013/0090378 A1    Apr. 11, 2013

Related U.S. Application Data

(60) Provisional application No. 61/295,469, filed on Jan. 15, 2010.

(51) Int. Cl.
| | | |
|---|---|---|
| *A61K 36/45* | (2006.01) | |
| *C07D 407/14* | (2006.01) | |
| *A61K 31/352* | (2006.01) | |
| *C07D 311/60* | (2006.01) | |
| *C07D 311/62* | (2006.01) | |
| *B65B 1/04* | (2006.01) | |
| *A23L 1/30* | (2006.01) | |
| *A23L 2/52* | (2006.01) | |

(52) U.S. Cl.
CPC ............. *C07D 407/14* (2013.01); *A23L 1/3002* (2013.01); *A61K 31/352* (2013.01); *A61K 36/45* (2013.01); *B65B 1/04* (2013.01); *C07D 311/60* (2013.01); *C07D 311/62* (2013.01); *A23L 2/52* (2013.01)

(58) Field of Classification Search
None
See application file for complete search history.

(56) References Cited

U.S. PATENT DOCUMENTS

| | | |
|---|---|---|
| 2001/0012525 A1 | 8/2001 | Mann |
| 2001/0021398 A1 | 9/2001 | Walker et al. |
| 2003/0203962 A1 | 10/2003 | Howell et al. |
| 2004/0109900 A1 | 6/2004 | Sorokin |
| 2009/0035432 A1 | 2/2009 | Mantius et al. |

FOREIGN PATENT DOCUMENTS

| | | |
|---|---|---|
| CN | 101239962 | 8/2008 |
| RU | 2237488 C1 * | 10/2004 |
| WO | 02/087357 | 11/2002 |

OTHER PUBLICATIONS

Turi (Pharmaceutical Biology (1999), vol. 39, No. 2, pp. 127-133).*
Office Action issued in CN Application No. 201180011537.2 on Mar. 9, 2015 with English Translation (10 pages).
Office Action issued in CL Application No. 2012-001985 on Sep. 2, 2014 (8 pages).
Office Action issued in CN Application No. 201180011537.2 on Aug. 11, 2014 with English translation (11 pages).
International Search Report and Written Opinion dated May 6, 2011 for corresponding application PCT/US2011/021431.
Office Action issued in CN201180011537.2 on Mar. 26, 2014 with English translation (14 pages).
Office Action issued in CL2012-001985 on Nov. 13, 2013 (11 pages).
Office Action issued in CN Application 201180011537.2 on Sep. 6, 2015 with English Translation (19 pages).

* cited by examiner

*Primary Examiner* — Susan Hoffman
(74) *Attorney, Agent, or Firm* — Fish & Richardson P.C.

(57) ABSTRACT

Provided are methods of producing proanthocyanidin (PAC)-containing solutions, powders, and beverages, as are PAC-containing solutions, powders, and beverages produced thereby and cranberry plant material products.

30 Claims, 1 Drawing Sheet

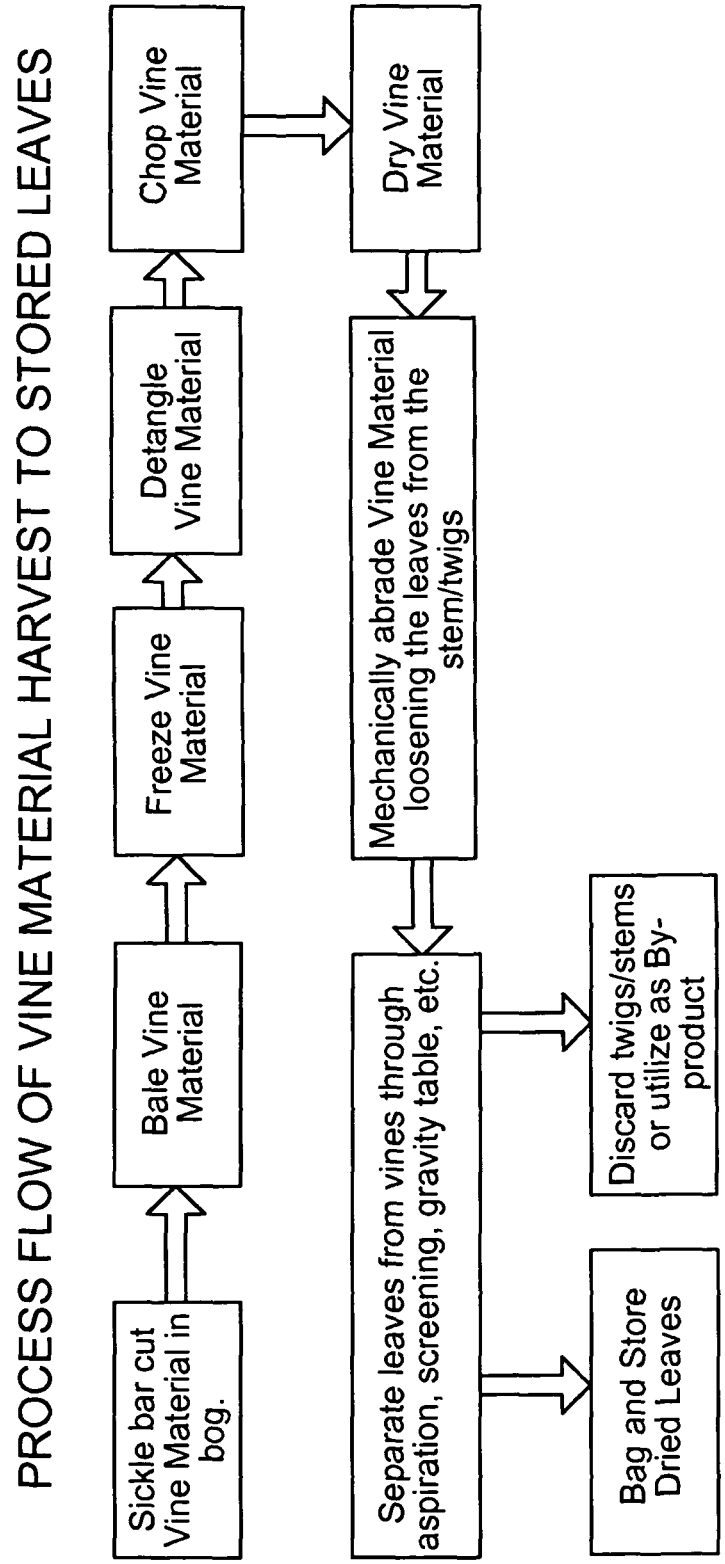

PROCESS FOR EXTRACTING COMPOUND FROM CRANBERRY LEAVES AND RELATED PRODUCTS

CROSS-REFERENCE TO RELATED APPLICATION

This application is a 371 US National of PCT/US2011/021431, filed Jan. 14, 2011, which claims priority to U.S. Application No. 61/295,469, filed on Jan. 15, 2010, the contents of which are hereby incorporated by reference in its entirety.

BACKGROUND

Certain fruits, particularly cranberries, contain a class of compounds known as Proanthocyanidins (PACs; also called procyanidins and condensed tannins). Cranberry and other members of the genus *Vaccinium* also contain various phenolic compounds and anthocyanins. PACs have antioxidant activity and interfere with adhesion of bacterial cells to epithelial cells. PACs are also thought to impart various health benefits. A number of processes are useful for isolating PACs from cranberries and other fruits. Additional methods for the selective capture and dry weight concentration of PACs will provide additional opportunities to prepare beverages and foods expected to have health benefits.

SUMMARY

Described herein are, inter alia, methods for obtaining PAC-containing extracts from cranberry leaves and vine material. Methods for preparing a beverage, e.g., a tisane, from cranberry leaves are also described. The methods can be used to obtain PAC-containing extracts that have a relatively high concentration of PACs and a relatively low concentration of sugars and acids. Sugars and acids are often present at high levels in PAC-containing extracts derived from cranberry fruit. Thus, when it is desirable to obtain an extract or product that is relatively low in sugar and/or acids, additional processing steps are often needed to reduce the amount of sugars and/or acids present in extracts of cranberries.

Accordingly, in one aspect, the present specification provides a method of producing a PAC-containing solution or a PAC-containing powder. The method includes providing a mixture of cranberry plant material (e.g., cranberry leaves and/or stems) and an aqueous medium, wherein the cranberry plant material is provided in the mixture in a range of about 1 to 12%, e.g., 5 to 10% (e.g., on a w/w basis); and steeping the material (e.g., leaves and/or stems) in the aqueous medium with or without enzymes, or an organic solution such as ethanol or propylene glycol solution, under conditions to extract PACs, thereby creating a PAC-containing solution; and optionally separating the steeped cranberry plant material (e.g., leaves and/or stems) from the PAC-containing solution. The cranberry plant material can include cranberry leaves and/or cranberry plant stems, e.g., at at least or about 20%, e.g., at least or about 30%, 40%, 50%, 60%, 70%, 80%, 90%, 95%, or at least or about 99% cranberry leaves or cranberry plant stems by weight. The cranberry plant material, e.g., leaves and/or stems, can optionally be dried at any time prior to steeping, e.g., to have less than about 70%, e.g., less than about 60%, 50%, 40%, 30%, 20%, 10%, or less than about 5%, moisture by weight. The method can include harvesting cranberry leaves from cranberry plants, drying the leaves, and optionally size-reducing the leaves, e.g., by grinding, to an average particle size of between about 0.05 mm and 5 mm, e.g., between about 0.1 mm and 2 mm, or 0.25 mm and 1 mm. Optionally, cranberry plant material, e.g., leaves and/or stems, can be frozen prior to drying. Cranberry plants, leaves, and/or stems for use in the present methods can be harvested at any time, e.g., in the spring (e.g., before cranberry fruits are formed) or fall (e.g., after cranberries are harvested from the cranberry plants). Cranberry plants, leaves, and/or stems for use in the present methods can be harvested during the cranberry plants' dormancy period. The methods can include clarifying the PAC-containing solution to produce a clarified PAC-containing solution and/or concentrating the PAC-containing solution, e.g., to at least or about 20% solids by weight, e.g., at least or about 30%, 40%, 50%, 60%, 70%, or at least or about 80%, or greater than 80%, solids by weight. The methods can include heating the proanthocyanidin-containing solution, e.g., to at least or about 185° F., e.g., at least or about 190° F., 195° F., 200° F., 205° F., or at least or about 210° F., for at least 10 minutes, e.g., at least 15, 20, 25, or 30 minutes. The methods can include processing (e.g., drying) the solution to provide a PAC-containing powder. For example, the method can include vacuum drying, freeze drying and/or drum drying the solution to form a powder. For example, the method can include spraying drying the PAC-containing solution, e.g., spraying the PAC-containing solution optionally onto a carrier, and then drying the carrier. In one embodiment, the method is performed in a batch process. In another embodiment, at least two, e.g., 3, 4, or 5, e.g., all steps of the method are performed in a continuous process. The continuous process can include grinding the cranberry leaves in the aqueous medium. The continuous process can also include stripping aroma from the cranberry leaves. In one embodiment, separating the steeped cranberry plant material (e.g., leaves and/or stems) from the proanthocyanidin-containing solution can include decanting the proanthocyanidin-containing solution to remove cranberry leaves. Separating the steeped cranberry plant material (e.g., leaves and/or stems) from the proanthocyanidin-containing solution can alternatively or additionally include centrifuging the proanthocyanidin-containing solution. Optionally, the continuous process includes, after separating the steeped cranberry plant material (e.g., leaves and/or stems) from the proanthocyanidin-containing solution, evaporating the proanthocyanidin-containing solution to a Brix content of about 40° to 60° Brix, e.g., 50° Brix.

In another aspect, the specification provides methods of producing a proanthocyanidin-containing solution in a continuous process, comprising providing a mixture of cranberry leaves and an aqueous medium, wherein the leaves are provided in the mixture at about 1-10%, e.g., 5-10% w/w; steeping the leaves in the aqueous medium under conditions to extract proanthocyanidins thereby creating a proanthocyanidin-containing solution; and separating the steeped leaves from the proanthocyanidin-containing solution, wherein all steps are performed in a continuous process. The continuous process can include grinding the cranberry leaves in the aqueous medium. The continuous process can also include stripping aroma from the cranberry leaves, e.g., at any step of the process. In one embodiment, separating the steeped cranberry plant material (e.g., leaves and/or stems) from the proanthocyanidin-containing solution can include decanting the proanthocyanidin-containing solution to remove cranberry leaves. Separating the steeped cranberry plant material (e.g., leaves and/or stems) from the proanthocyanidin-containing solution can alternatively or additionally include centrifuging the proanthocyanidin-containing solution. Optionally, the continuous process includes, after separating the steeped cranberry plant material (e.g., leaves and/or stems) from the proanthocyanidin-containing solution, evaporating the proanthocyanidin-containing solution to a Brix content of about 40° to 60° Brix, e.g., 50° Brix.

In another aspect, the specification provides a method for preparing a beverage, comprising producing a PAC-containing solution or powder according to the methods described herein and combining the PAC-containing solution or powder, or a fraction derived therefrom, with one or more additional components, e.g., water, a juice, a sweetener, a natural or artificial flavor, or a tisane, or any combination thereof, to thereby produce a beverage.

In still another aspect, the specification provides a product comprising cranberry plant material disposed within a container, the container having a volume, wherein the cranberry plant material comprises at least or about 40%, e.g., at least or about 50%, 60%, 70%, 80%, 90%, or at least or about 99%, cranberry leaves or cranberry leaf fragments by weight and occupies at least or about 20%, e.g., at least or about 30%, 40%, 50%, 60%, 70%, 90%, 95%, or at least or about 99% of the volume of the container. Depending upon the amount of cranberry leaves present in the cranberry plant material, the cranberry plant material may also comprise cranberry plant stems, e.g., at least or about 1%, e.g. at least or about 5%, 10%, 20%, 30%, 40%, 50%, or at least or about 60% cranberry plant stems. The container can be configured to allow a solution to flow through the container and contact the cranberry plant material and/or comprised of material that allows a solution to flow through the container and contact the cranberry plant material. The product may optionally comprise within the container at least one further component, e.g., water; tea leaves or fragments thereof; a natural flavoring composition; an artificial flavoring composition; a natural or artificial sweetener; and acidulant; a vitamin composition; an amino acid composition; and/or a mineral composition.

In yet another aspect, the specification provides a product comprising cranberry plant material disposed within a container, the container having a volume, wherein the cranberry plant material comprises at least or about 40%, e.g., at least or about 50%, 60%, 70%, 80%, 90%, or at least or about 99%, cranberry plant stems or cranberry plant stem fragments, by weight and occupies at least or about 20%, e.g., at least or about 30%, 40%, 50%, 60%, 70%, 90%, 95%, or at least or about 99% of the volume of the container. Depending upon the amount of cranberry plant stems present in the cranberry plant material, the cranberry plant material may also comprise cranberry plant leaves, e.g., at least or about 1%, e.g. at least or about 5%, 10%, 20%, 30%, 40%, 50%, or at least or about 60% cranberry plant stems. The container can be configured to allow a solution to flow through the container and contact the cranberry plant material and/or comprised of material that allows a solution to flow through the container and contact the cranberry plant material. The product may optionally comprise within the container at least one further component, e.g., water; tea leaves or fragments thereof; a natural flavoring composition; an artificial flavoring composition; a natural or artificial sweetener; and acidulant; a vitamin composition; an amino acid composition; and/or a mineral composition.

In still another aspect, the specification provides a method of making a product comprising cranberry plant material disposed within a container, comprising providing a container having a volume; providing cranberry plant material (e.g., cranberry leaves and/or stems); and disposing the cranberry plant material into the container such that the cranberry plant material occupies at least about 20%, e.g., at least or about 30%, 40%, 50%, 60%, 70%, 90%, 95%, or at least or about 99% of the volume of the container.

In another aspect, the specification provides a tea bag, wherein the tea bag has a volume and comprises cranberry plant material (e.g., leaves and/or stems), and wherein the cranberry plant material occupies at least or about 20%, e.g., at least or about 30%, 40%, 50%, 60%, 70%, 90%, 95%, or at least or about 99% of the volume of the tea bag. For example, the cranberry plant material can comprise at least or about 40%, e.g., at least or about 50%, 60%, 70%, 80%, 90%, or at least or about 99%, cranberry leaves or cranberry leaf fragments, or cranberry plant stems or cranberry plant stem fragments, by weight. The cranberry plant material can comprise a mixture of cranberry leaves and cranberry plant stems.

In another aspect, the specification provides a PAC-containing solution or powder, wherein the solution is made by a process comprising providing a mixture of cranberry plant material (e.g., cranberry leaves and/or cranberry plant stems) and a medium (e.g., water and/or an alcohol), wherein the cranberry plant material is present in the medium in a range of about 5 to 10% (e.g., on a w/w basis); steeping the cranberry plant material under conditions sufficient to extract proanthocyanidins from the cranberry plant material; and separating the steeped cranberry plant material from the medium, to thereby produce the PAC-containing solution. The PAC-containing solution can include another component described herein, e.g., a flavoring. The PAC-containing solution can be further processed (e.g., dried) to form a PAC-containing powder.

In still another aspect, the specification provides a PAC-containing solution or powder produced by the methods described herein. For example, the PAC-containing solution can comprise PACs/total polyphenols in the range of about 0.5 to 1.5, total organic acids in a range of about 4% to 6% (dwb), and anthocyanins in a range of about 0.05% to 0.20% (dwb). Any PAC-containing solutions or powders described herein can further include any other component as described herein, e.g., a natural flavoring composition; an artificial flavoring composition; a natural or artificial sweetener; and acidulant; a vitamin composition; an amino acid composition; and/or a mineral composition.

In yet another aspect, the specification provides methods of reducing adhesion of a bacterial cell in a subject, e.g., in the urinary tract of a subject, wherein the method includes providing a composition comprising at least or about 10% proanthocyanidin by weight, wherein at least or about 40% proanthocyanidins are 10-mers or greater; less than or about 16% organic acids; and less than or about 20% sugars; and administering a therapeutically effective amount of the composition to the subject, thereby reducing adhesion of the bacterial cell, e.g., in the urinary tract of the subject. The described methods can be used to reduce adhesion of a bacterial cell in a urinary tract of a mammal, e.g., human and other animals, such as laboratory animals, e.g., mice, rats, rabbits, or monkeys, or domesticated and farm animals, e.g., cats, dogs, goats, sheep, pigs, cows, or horses. Any of methods described herein can be used to provide the composition for administration to the subject.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and from the claims.

DESCRIPTION OF DRAWING

FIG. 1 depicts a flowchart illustrating an example of a process for harvesting and preparing cranberry plant material.

DETAILED DESCRIPTION

The present invention is based, at least in part, on the finding that cranberry plant material, such as cranberry leaves and stems, comprise substantial amounts of PACs and can be extracted using the methods described herein. The term "cranberry plant material" means parts of a cranberry plant, e.g., cranberry leaves, stems, vines, or any other part of the cranberry plant other than cranberry fruits. Accordingly, the present specification provides, inter alia, methods of producing PAC-containing solutions (alternatively referred to herein as "extracts") and beverages from the cranberry plant material, PAC-containing solutions and beverages produced using such methods, and containers that comprise cranberry plant material, i.e., cranberry plant leaves and/or stems, such as tea bags comprising cranberry plant material.

Cranberry plants of any species or variety can be used in the methods described herein. For example, *Vaccinium oxycoccus, Vaccinium vitis-idaea* and/or *Vaccinium macrocarpon* can be used. *Vaccinium oxycoccus* (Common Cranberry or Northern Cranberry), and *Vaccinium vitis-idaea* (lingonberry or mountain cranberry) are widespread throughout the cooler portion of the Northern Hemisphere, including northern North America, northern Europe, and northern Asia. *Vaccinium oxycoccus* has small 5-10 mm leaves. The flowers are dark pink, and the fruit is a small red berry having a pleasantly sharp acidic flavor. *Vaccinium macrocarpon* (Large cranberry or American Cranberry) is native to northeastern North America and resembles *Vaccinium oxycoccos*, but has somewhat larger leaves and larger fruit. *Vaccinium vitis-idaea* has a more erect growth habit than the other two species and produces its tart, red fruit in determinant clusters. These varieties of cranberry plants can be used, as can any other known cranberry plant. Further, skilled practitioners will appreciate that a cranberry plant can be grown in a way that optimizes leaf production, i.e., to increased vegetative growth to provide longer stems and/or more leaves per plant as compared to cranberry plants grown under other conditions. Skilled practitioners will appreciate that the methods described herein can include using such optimized cranberry plants and/or steps that include optimizing cranberry plant vegetative growth.

Processing of Cranberry Plant Material

Commercial cranberry beds are often pruned or mowed in the spring or fall as part of routine maintenance of the beds. Vines collected during this harvesting, or during any other period, can be used in the methods of the invention. Since the level of PACs present in the leaves and stems can vary throughout the year and with variety, it can be desirable to select a time for harvesting leaves that provides a desired level of PACs. For example, one useful time for harvesting cranberry plant material (e.g., leaves and/or stems) in the present invention is when the cranberry plant enters the dormancy period, e.g., at any time during the dormancy period. In addition, it can be desirable to harvest the vines when any applied pesticide and herbicide residues are at a relatively low level and/or to harvest vines grown in regions or areas that require less (e.g., no) pesticide and/or herbicide.

Vines and attached leaves (also referred to as "vine material") can be harvested, for example, by hand or machine, typically using a sickle or rotary blade adjustable mower to cut the vines. Vine material is then picked up and formed into a bale (similar to a hay bale) using a commercial baler for ease of handling. Cut vine material may also be loaded into bins, hoppers, trucks or other forms of storage/conveyance to remove the material from the bog and transport to the point of storage or use. The vine material can then be frozen for later processing, dried at the field, and/or processed within a few days of harvest at ambient conditions.

The vine material can be size reduced and/or dried. Typically, cranberry vines are from 10 to 30 inches in length and tend to be extremely intertwined, matted and tangled. Vine material can be size reduced by any method, e.g., through a chopper (e.g., a Dauenhauer Chopper). However, for case of handling, the vine material can be passed through a detangling system. Detangling of the vine material facilitates loading into and flow through the chopper. An example of equipment useful for detangling is a Perrault Harvestor. For ease of handling, the vine material can be chopped to vine length of 1 to 8 inches. Vine material can be frozen or kept at ambient temperature when it is chopped. Vine material can be dried prior to chopping. Alternatively, vine material can be dried after chopping or can be partially dried before chopping and further dried after chopping. For drying, the chopped material can be conveyed to a batch, semi-continuous or continuous dryer, e.g., a box dryer, tunnel/rotary dryer, bed dryer, microwave dryer, etc. Drying conditions can be determined by a skilled practitioner. For example, drying conditions can range from 20 to 600 minutes or more, e.g., about 8 to 10 hours, at 60 to 200° F. and a relative humidity of, e.g., about 15% to 100%. Moisture content of the dried material can be, e.g., less than or about 20%, e.g., less than or about 10%, 5%, 3%, 2%, or less than or about 0.5%, e.g., to a range of about 0.5% to about 7%. Drying the material to a moisture content less than about 10% may facilitate separation of the leaves from the stems. After drying, cranberry leaves can be separated, e.g., mechanically, from the vine stems or twigs using any method known in the art, e.g., through mechanical shaking or abrasion using, e.g., a Bratney Brush Machine (Bratney Companies, Des Moines, Iowa), or through methods specifically designed to separate leaves from stems or twigs. Several mechanical steps can be employed to separate the leaves from the vine stems/twigs as well as other foreign material that might be in the harvested vine material, e.g., aspiration, screening, indent cylinders, and/or gravity tables, etc. The separation step to separate the twig/vine material and foreign matter can achieve, for example, a leaf purity of about or at least 20%, e.g., at least or about 60%, 70%, 80%, 90%, 99%, or greater than 99%, by weight. Separated leaves can be stored at low temperature and low humidity or at ambient dry conditions.

As an alternative to drying the vine material below about 10% moisture content, separation of leaves from the vine can be facilitated by freezing the vine material to below about –20° F. This technique may be used on wet vine material. Leaves can be separated from the vines by hand and/or mechanically using, e.g., a Bratney Brush Machine. Subsequently, the leaves can be subjected to cleaning steps, dried and/or frozen to assure stability and/or to achieve a greater than 80%, e.g., greater than or about 90%, 95%, 98%, or greater than or about 99% purity of leaves by weight.

Production of Proanthocyanidin Solutions and Beverages

PACs and other substances can be extracted from cranberry plant material, e.g., cranberry leaves and/or cranberry plant stems, for example, by grinding, then steeping the material in an aqueous solution with or without enzymes, e.g., at a pH range of about pH 2 to 14, e.g., about 2 to about 6.9, or about 7.1 to about 14. For example, the pH range can be about 2 to about 5 or about 9 to about 14. The aqueous solution can include, e.g., water or an organic solution such as an alcohol, e.g., ethanol, methanol, propanol, or propylene glycol solution, or any mixtures of alcohols. For example, water can be used, e.g., at 70° F. to 250° F. Skilled practitioners will appreciate that the period of time during which steeping is performed can vary depending upon the application. Methods of steeping are known in the art and include, e.g., countercurrent extraction, kettle brewing, percolation, and any combinations of such methods. Steeping can be performed, e.g., for 1 to 60 minutes, e.g., for at least or about 1, 5, 10, 20, 30, or at least 60 minutes. Steeping may be performed for longer periods of time if desired, e.g., at least or about 1, 2, 3, 5, 10, 20, or more than 20 hours. Multiple steeping steps can also be performed, where a plant material-solution mixture is steeped and optionally pressed, rehydrated in the same or different solution, and then steeped and optionally pressed again. This process can be repeated 1, 2, 3, 5, 8, or 10 times to extract more PACs from the plant material.

A variety of ratios of leaves and/or stems to solution can be chosen within the limit of the process. For example, a leaf and/or stem to solution ratio of about 1:10 w/w is useful, as are ratios of about 1:15 and about 1:20. Ranges of about 0.5%-20% (w/w) leaves and/or stems in solution, e.g., about 1%-20%, or about 5%-15%, e.g., about 10% (w/w) leaves and/or stems, are also useful.

Aroma can be removed or stripped from cranberry plant material, e.g., cranberry leaves and/or cranberry plant stems, for example, by methods known in the art. Exemplary methods include the spinning cone technique, vacuum distillation, and steam distillation. Aroma stripping can be performed at any step of the process. For example, aroma stripping can be performed on the leaves and/or stems prior to any step of extraction and/or on solutions during the extraction process. Skilled practitioners will appreciate that a plant material-solution mixture can be stripped of aroma, steeped, and pressed multiple times, e.g., 2, 3, 5, 8, and 10 times or more, to remove aroma, extract more PACs, and produce a decreased aromatic extract, with low flavor. The decreased aromatic extract can optionally be supplemented with flavoring (e.g., natural and/or artificial sweeteners).

Optionally, the bulk of the insoluble solids can then be removed from the solution by any method, e.g., by filtration, decanting, pressing and/or centrifugation. The solution can if desired be further clarified by other filtration methods, e.g., ultrafiltration, and optionally, flavor components can be removed by steam distillation. The solution can be concentrated e.g. to at least or about 20%, e.g., at least or about 30%, 40%, 50%, or greater than 50% solids. The solution can be pasteurized, e.g., by heating to 185° F. for 10 minutes before filtration and concentration. Alternatively or in addition, the solution and/or the byproducts from this process can be extracted or purified by chromatography, adsorbent resin (e.g., in a resin column), sedimentation and/or membrane technology (e.g., ultrafiltration, nanofiltration, or reverse osmosis) to yield cranberry plant-related compounds.

The concentrated solution can be combined with water, juices and/or other flavorings (e.g., natural and/or artificial sweeteners) to create a beverage. The concentrated solution can be vacuum dried, spray dried, freeze dried, or drum dried, etc., with or without a carrier and dried to form a powder. The powder can be added to water, juices, foods or flavorings to create a variety of products. The dried powder either on its own or combined with other dried ingredients can be used to prepare an instant beverage. Thus, the dried powder can be sold in bulk or in single serving packs.

The processes described above can be performed in a batch, semi-continuous, or continuous process. In one embodiment, the methods described herein, e.g., providing cranberry plant material (e.g., cranberry leaves and/or stems), steeping the material in a solution (e.g., water or organic solution), and separating the steeped material from the solution, are performed in a continuous-flow system at steady-state equilibrium. For example, continuous process management can be adapted to suit all operating steps described in the present specification, where cranberry plant material is, for example, disposed in a hopper, mixed with a solution, ground in a grinder, transferred to a tank, heated (e.g., to 85° C. or above) with a heat exchanger, stripped of aroma, held in a tank for about 26 to 30 minutes, decanted to remove large particles, centrifuged to remove fine particles, and evaporated to a desired Brix content, e.g., about 400 to about 60° Brix, e.g., 50° Brix. Skilled practitioners will appreciate that one or more steps in the continuous process can be repeated multiple times. Skilled practitioners will also appreciate that not all aforementioned steps need be performed in a given process, e.g., in one or more cycles of the process.

Solutions and Cranberry Plant Material Products

Solutions, Powders, and Beverages

The present specification also provides PAC solutions, powders and beverages produced as described above. The PAC solutions of the present invention include, inter alia, PACs that are naturally produced by cranberry plants, i.e., in the leaves and/or stems of cranberry plants. Skilled practitioners will appreciate that PACs are a form of flavonol that are composed of polymer chains of catechins and/or epicatechins. PACs differ in the nature of their constitutive units, sequence, the position of interflavanic linkages, chain length, and the presence of subunits (e.g., galloyl or glucosyl groups and flavonoids). Thus, the chemical profile of a PAC from one source may differ from the chemical profile of a PAC from another source. The PACs present in the PAC solutions of the present invention can be characterized, e.g., as having a mean degree of polymerization between 4 and 6, with a range of anywhere between a single molecule to polymer chains with over 20 linked monomers, with approximately 15-25% Type A linkages in addition to the more commonly found Type B linkages. The content of PACs in cranberry leaves is about 25-60 mg/g dry weight basis (dwb) and the content in an extract produced from the leaves, e.g., in an extract produced by steeping 1-12% leaves in a medium (w/w), can be in a range of about 125-750 mg/g dwb. The degree of polymerization of PACs found in cranberry fruit and leaves are similar in that about 40 to 70% of the PACs are large polymeric PACs with chain lengths of 10 or more, but different from extracts produced from juice which have about 20-50% PACs larger than 10-mers. Extracts produced from cranberry leaves, e.g., in 5-10% w/w solutions can have, e.g., a profile of PACs of about 40-70% polymeric PACs that are 10-mers or greater than 10-mers. For example, extracts produced from cranberry leaves can have greater than or about 40%, 50%, 60%, 70%, or greater than or about 80% 10-mers or greater than 10-mers. Extracts produced from tea leaves (e.g., *Camellia sinensis*) can have greater than 90% PACs that are smaller than 10-mers. The quantities of flavonoids (e.g., phenolic acids, flavanols, and anthocyanins) of leaf and fruit are quite different. For example, anthocyanins in leaf are 0.05-1.0% which is much lower than the anthocyanins in fruit extracts (e.g., 2-11%).

Skilled practitioners will also appreciate that the PAC solutions of the present invention can be characterized in terms of the percentage of PACs in the PAC solutions, e.g., on a dry weight basis. The amount of PACs can be detected using any known method, e.g., HPLC and/or the dimethylaminocinnamaldehyde (DMAC) method (see, e.g., Cunningham, D. G.; Vannozzi, S.; O'Shea, E.; Turk, R., Analysis and standardization of cranberry products. In *Quality management of nutraceuticals*, ACS Symposium Series 803 ed.; American Chemical Society: Washington, D C, 2002; pp. 151-166). For example, the PAC solutions of the present invention can comprise at least or about 10%, e.g., at least or about 15%, 20%, 25%, 30%, 35%, 40%, 45%, 50%, 55%, 60%, 70%, 80%, 90% or at least or about 99%, or more than 99%, or a range between any two of these values, PACs.

Alternatively or in addition, skilled practitioners will appreciate that the PAC solutions of the present invention can be characterized according to the levels of organic acids (e.g. total organic acids) and/or sugars (e.g., total sugars) in the solution (e.g., on a dry weight basis). For example, solutions can contain less than or about 20% organic acids (e.g., less than or about 16%, 14%, 10%, 8%, 5%, 4%, 3%, 2%, or less than or about 1% organic acids, or no organic acids (e.g., the extract can be free (e.g., substantially free) of organic acids), or a range between any two of these values, and/or less than or about 20% sugars (e.g., less than or about 15%, 10%, 5%, 3%, 2%, 1% sugar, or no sugar (e.g., the extract can be free (e.g., substantially free) of sugar), or a range between any two of these values. Alternatively or in addition, the PAC solutions can be characterized according to the ratio of PACs to other solution components, such as organic acids and/or sugars (e.g., on a dry weight basis). For example, PAC solutions of the present invention can include cranberry plant material-derived PACs and organic acids in a ratio of about 4:1 (PACs: organic acids), e.g., about 5:1, 6:1, 8:1, 10:1, 3:1, 2.5:1, 2:1, 1.5:1 or about 1:1, or in a range between any two of such ratios. As another example, PAC solutions of the present invention can include cranberry plant material-derived PACs and sugars in a ratio (PACs:sugars) of about 3:1, 2:1, 2.5:1, 4:1, 4.5:1, 5:1, or in a range between any two of such ratios. Alternatively or in addition, the solution can be characterized by the ratio of PACs to total phenolic content or to other specific flavonoids such as phenolic acids, and flavanols or the PAC ratio to anthocyanin which is uniquely low in the leaf and stem. For example, the solutions of the present invention can include cranberry plant material-derived PACs and total polyphenolic content (as measured using methods known to those of ordinary skill in the art) in a ratio of about 1:1 (PAC:total polyphenols), e.g., about 1:1.5, 1:8, 1:2, or about 1:2.5 or in a range between two such ratios. As another example, the PAC solution can include PAC:phenolic acids ratio of 15:1, 20:1, 25:1, 30:1, or about 35:1 or PAC to anthocyanin ratio of about 150:1, 200:1, 250:1, or about 300:1. In particular embodiments, the PAC to organic acid ratio is 3:1 and PAC to sugar ratio is about 2:1. Skilled practitioners will appreciate that higher ratios of PACs to organic acids and/or sugars are possible.

Methods described herein, e.g., involving providing cranberry plant material (e.g., cranberry leaves and/or stems), steeping the material in a medium (e.g., an aqueous medium or organic solution), and optionally, separating the steeped material from the medium, result in an extract, i.e., a PAC-containing solution, that may be referred to by skilled practitioners as a "single strength" extract or PAC-containing solution. Such single strength extracts or solutions are typically not subjected to concentration or manipulation of components following separation from steeped material. Single strength extracts or PAC-containing solutions are within the present invention among other PAC-containing compositions, e.g., solutions and powders. For example, the present invention includes a single strength PAC-containing solution made from steeping cranberry leaves in water in a range of about 1 to 12% (w/w), e.g., 5-10%, wherein the solution comprises PACs/total polyphenols in the range of about 0.5 to 1.5, total organic acids in a range of about 4% to 6% (dwb), and anthocyanins in a range of about 0.05% to 0.20% (dwb).

Cranberry Plant Material Products

The present specification also provides a variety of cranberry material products. For example, included within the present invention is a container comprising cranberry plant material. The cranberry plant material disposed within the container can comprise cranberry leaves, cranberry plant stems, or mixtures thereof. One or more components of the material, e.g., all components of the material, can be dried or in its naturally hydrated state and/or reduced in size from its natural state, e.g., broken, ground, shredded and/or crushed. For example, the cranberry plant material can be comprised of components that have been subjected to size reduction, e.g., shredding, and are of a size of less than 5 mm, e.g., less than 1 mm. In some embodiments, the cranberry plant material consists essentially of cranberry leaf fragments and/or cranberry plant stem fragments, wherein most, e.g., at least or about 80%, e.g., at least or about 90%, of the fragments range in size from about 0.01 mm to 5 mm, e.g., about 0.1 mm to 3 mm, 0.2 mm to about 2 mm, 0.25 mm to 1 mm, e.g., about 1 mm to 2 mm. Skilled practitioners, such as those skilled in the art of making tea products, will appreciate that fragment sizes outside of these ranges are possible and are clearly within the present invention.

The cranberry plant material can comprise cranberry leaves, at at least or about 5% by dry weight, e.g., at least or about 10%, 20%, 30%, 40%, 50%, 60%, 70%, 80%. 90%, or at least or about 99% cranberry leaves by weight. As another example, the cranberry plant material can comprise cranberry plant stems at at least or about 5% by weight, e.g., at least or about 10%, 20%, 30%, 40%, 50%, 60%, 70%, 80%, 90%, at least or about 99% cranberry plant stems by weight. Where the cranberry plant material includes a mixture of cranberry leaves and cranberry plant stems, any mixture or ratio of cranberry leaves and cranberry plant stems by weight is contemplated. For example, the ratio of cranberry leaves to stems can be about 10,000:1, 5,000:1, 1000:1, 500:1, 100:1, 50:1, 10:1, 5:1, or about equal, i.e., 1:1, or can range between any two of such ratios. The ratio can be reversed, i.e., wherein the ratio of cranberry plant stems to leaves is about 10,000:1, 5,000:1, 1000:1, 500:1, 100:1, 50:1, 10:1, 5:1, or about equal, i.e., 1:1, or can range between any two of such ratios.

The container has a volume at least partially occupied by the cranberry plant material. For example, at least or about 5% of the volume of the container, e.g., at least or about 10%, 15%, 20%, 25%, 30%, 50%, 60%, 75%, 90%, 95%, or at least or about 99%, greater than 99%, or 100%, can be occupied by the cranberry plant material.

Optionally, one or more additional components may be included within the container. Such a component can be, e.g., any component that may enhance or provide flavoring and/or enhance or provide nutritional value to a beverage produced using the product, and/or that may preserve freshness and prevent spoilage. For example, the additional component can include, but is not limited to, another plant component (such as tea leaves or fragments thereof or ginseng), a flavor composition, (e.g., a natural or artificial flavoring composition, such as a fruit juice powder, or natural or artificial sweetener), a vitamin, a mineral, an amino acid, a preservative, or acidulant, e.g., citric acid, or any combination thereof.

The container can be, e.g., any container of any size capable of holding cranberry plant material, e.g., a bag, sack, tub, pouch or packet of any size. For example, the container can be a tea bag. Tea bags and methods of making tea bags, e.g., comprising plant materials such as tea, are well known in the art. Skilled practitioners will appreciate that such methods can be easily adapted to create a tea bag that comprises the cranberry plant material described herein. The container can be made of any materials deemed appropriate for the container's intended use. For example, for tea bags, the material could be any that are traditionally used for such a purpose, e.g., a material that allows a solution, such as water, to pass through the material and contact the cranberry plant material. Alternatively, where a larger container is needed, the container can made of stronger material, such as plastic, burlap or canvas. The container can be made of any material appropriate for storing and/or shipping cranberry plant material.

Methods of Treatment

The present specification provides PAC-containing solutions and powders to reduce or inhibit adhesion of a bacterial cell in a urinary tract of a subject. Reduction or inhibition of adhesion of a bacterial cell in the urinary tract can, for example, reduce or inhibit urinary tract infections (UTIs). UTI is a bacterial infection that affects any part of the urinary tract, e.g., in humans, the urinary tract comprises two kidneys, two ureters, a bladder, a urethra, and two sphincter muscles. One causal agent of UTI is *Escherichia coli*. If pathogenic bacteria get into the bladder or kidney and multiply in the urine, they may cause a UTI.

Subjects to be Treated

A subject can be selected on the basis that they have, or are at risk of developing, a UTI. It is well within the skills of an ordinary practitioner to recognize a subject that has, or is at risk of developing, a UTI. A subject that has, or is at risk of developing UTI is one having one or more symptoms of the condition or one or more risk factors for developing the condition. Symptoms of UTI are known to those of skill in the art and include, without limitation, frequent feeling and/or need to urinate, pain during urination, and cloudy urine. A subject that has, or is at risk of developing, UTI is one with known risk factors such as sex (e.g., women are more prone to UTIs than men), frequency of sexual intercourse, diabetes, sickle-cell disease, or anatomical malformations of the urinary tract, e.g., prostate enlargement.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

Methods of Administration

In general, and as far as efficacy is concerned, oral administration is suitable. For instance, PAC-containing solutions and powders can be administered in beverages (e.g., tea, water, milk, juice, soda, and other flavored liquids). PAC-containing solutions can be taken by adding an additive such as a sweetener if necessary. Additionally, various methods can be used when combining PAC-containing solutions with conventional beverages and foods. In such cases, the amount of PAC-containing solution used can be appropriately adjusted according to an individual's eating and drinking habits.

These dosages can be administered as a single bolus or as an infusion over one or more hours or days. Further, PAC-containing solutions can be administered at the same time and length as antibiotic treatment or every day for subjects who have, or at risk of developing, a UTI. Optimal dosage levels can be readily determined by a skilled practitioner, such as a physician, e.g., a urologist. Exemplary dosages include, e.g., about 50 mg a day, about 100 mg a day, about 150 mg a day, about 200 mg a day, about 250 mg a day, about 300 mg a day, about 400 mg a day, about 500 mg a day, about 600 mg a day, and about 1000 mg a day.

The invention will be further described in the following examples, which do not limit the scope of the invention described in the claims.

EXAMPLES

Example 1

Preparation of Extract

Cranberry vine material can be removed from the bog, frozen, and/or dried and chopped. The leaves can be removed from the vine material and size reduced (e.g., chopped). An aqueous slurry is prepared at various leaf to water ratios, e.g., 1:10 w/w, heated to 212° F. for various hold times, filtered through Whatman filter paper, and the extract can be analyzed for PACs, total polyphenols, sugars, acids, pesticides, and total microbiological plate count. This extract can then be prepared with flavor, sugar and acid for a ready to drink tea.

Example 2

Preparation of Extract

Cranberry vine material can be removed from the bog, frozen, and/or dried and chopped. The leaves can be removed from the vine material and size reduced (e.g., chopped). A propylene glycol/aqueous slurry is prepared at various leaf to solution ratios, and the flavor components extracted. This flavor component is then added to the extract from Example 1 to create a more robust ready to drink tea flavored beverage.

Example 3

Preparation of Extract

Cranberry vine material can be removed from the bog, frozen, and/or dried and chopped. The leaves are removed from the vine material and size reduced (e.g., chopped). An about 500 lb. aqueous slurry is prepared at various leaves to water ratios, e.g., a 1:10 leaf to water ratio, and passed through a steam distillation column at atmospheric pressure or under vacuum to remove the aroma. The slurry is then cooled immediately and sent through the solid removal process. The extract is then further clarified or concentrated and ready for the spray dryer or as the addition to the ready to drink beverage as a PAC source.

Example 4

Comparison of Extract Prepared from Leaves to Cranberry Juice and Various Cranberry Derived Extracts The level of PACs and various other components in an extract prepared from leaves was measured and compared to cranberry juice and various extracts prepared from cranberries. As detailed in Table 1 below, an exemplary extract prepared from leaves had a higher concentration of PACs and a lower concentration of measured sugars and organic acids on a dry weight basis than did the various cranberry fruit-derived extracts.

The leaf extract had only about 5-8 grams measured organic acids (quinic, malic, citric and galacturonic) per 100 grams total dry weight compared to about 39-42 grams for cranberry juice. The level of measured sugars (dextrose, fructose, and sucrose) was also lower, about 20 grams compared to 48 grams (dry weight basis per 100 grams total). However, the level of PACs was much higher in the leaf extract, about 30 grams compared to 3 grams (dry weight basis per 100 grams total) as was the level of phenolics—about 30 grams for the leaf extract compared to 4 grams for the cranberry juice.

Thus, for each 100 mg of PACs, the leaf extract has only 35 mgs of total measured acids and only 143 mg of total measured sugars, compared to 1225 mg and 1641 mg, respectively for cranberry juice.

TABLE 1

| Component | Cranberry Powder (% DWB) | Cranberry Leaf Extract (% DWB) |
| --- | --- | --- |
| Carbohydrates (calc. by difference) | 92.11 | 70.49 |
| Organic Acids | 41.07 | 5.80 |
| Sugars | 47.63 | 19.40 |
| Fiber | 6.21 | <1.0 |
| Protein | <0.10 | 1.29 |
| Fat | 0.25 | 0.83 |
| Ash | 7.69 | 4.06 |
| Phenolics | 3.97 | 29.20 |
| PACs | 3.45 | 30.80 |
| Anthocyanins | 0.22 | 0.05 |
| Moisture | — | — |

Example 5

Anti-Adhesion Properties

To determine the anti-adhesion strength of cranberry products, a cranberry dried extract with 2 mg or 4 mg of PACs was diluted in 1 mL of a phosphate buffer solution (PBS). The buffered cranberry solution was added to P-fimbriated *E. coli* and mixed with red blood cells. Anti-adhesion bioactivity was measured by counting the amount of agglutination of red blood cells in the presence of *E. coli* and cranberry product. If minimal agglutination was observed, the strength of the cranberry material was halved by serial dilution and agglutination was observed again. This procedure was repeated until 50% agglutination was observed, at which point, the endpoint is determined. (The lower the dilution, the more active the sample.) The concentration of cranberry material at the endpoint is reported as the bioactivity endpoint. Generally, a standard deviation of one dilution is typical for the assay.

TABLE 2

| Sample | Whole Product A/A | Concentrated A/A |
| --- | --- | --- |
| 495 | Negative | Dilution 5 |
| 664 | Negative | Negative |
| 841 | Negative | Dilution 6 |

Summary: Sample 841 (200 mg PACs/15.2 oz) was twice as active as Sample 495 (100 mg PACs/15.2 oz). Sample 664 was a placebo with no PACs.

Example 6

Anti-Adhesion Properties

Beverages were prepared with cranberry dried extract as described herein to deliver 100 or 200 mg PACs in 15.2 ounces. Anti-adhesion activity of human urine after the consumption of the cranberry beverages was compared against a placebo beverage that does not contain cranberry dried extract. In this double blind placebo-controlled crossover study, all subjects consumed all products with a one week washout period in between each different product. Healthy, middle-aged subjects (n=10) without a history of current or recurrent urinary tract infections, antibiotic use within the last six months, history of urinary disorders, allergy or adverse reaction to cranberry products were recruited from the Marucci Center for Blueberry/Cranberry Research. Prospective subjects' urines were screened for production of endogenous bacterial anti-adhesion activity prior to recruitment. If endogenous inhibitors were detected, these subjects were excluded from participation in the trial.

Pre-Visit Subject Preparation: Dietary restrictions—refrain from consuming all cranberry and blueberry products for a seven day wash out period prior to consuming test products and throughout test period.

Study Design: On urine collection days, additional fluid consumption standardized volunteers to 240 mL every 3 hours to avoid dilution of urine samples and allow for detection of anti-adhesion activity, if present.

On day 1, urine (approximately 25 mL) was collected (clean-catch) from each participant prior to product consumption. This pre-consumption urine sample was immediately frozen at −80° C. That afternoon/evening, each participant consumed one 15.2-oz bottle of test beverage. The next morning, (12 hours after the evening dose), participants were administered a second 15.2-oz bottle of the same test beverage. Urine was collected at 0-3 hour, 3-6 hour, 6-9 hour, and at 24 hours post-consumption time. Urine collected during each 3 hour time period was pooled for each participant and immediately frozen at −80° C.

Urine was tested for anti-adhesion activity using the method described in Example 5 and results are shown in Table 3.

TABLE 3

| Subject | Sample | Background | 0-3 hrs | 3-6 hrs | 6-9 hrs | 24 hrs |
| --- | --- | --- | --- | --- | --- | --- |
| 1F | 495 | 0 | 1 | 1 | 0 | 2 |
| 2F | 495 | 0 | 0 | 0 | 0 | 0 |
| 3F | 495 | 0 | 1 | 0 | 0 | 2 |
| 4F | 495 | 0 | 0 | 0 | 0 | 0 |
| 5F | 495 | 0 | 2 | 1 | 0 | 0 |
| 6F | 495 | 0 | 0 | 0 | 0 | 0 |
| 7M | 495 | 0 | 0 | 0 | 0 | 0 |
| 8M | 495 | 0 | 0 | 0 | 0 | 0 |
| 9M | 495 | 0 | 0 | 0 | 0 | 0 |
| 10M | 495 | 0 | 0 | 0 | 0 | 0 |
| 1F | 664 | 0 | 0 | 0 | 0 | 0 |
| 2F | 664 | 0 | 0 | 0 | 0 | 0 |
| 3F | 664 | 0 | 0 | 0 | 0 | 0 |
| 4F | 664 | 0 | 0 | 0 | 0 | 0 |
| 5F | 664 | 0 | 0 | 0 | 0 | 0 |
| 6F | 664 | 0 | 0 | 0 | 0 | 0 |
| 7M | 664 | 0 | 0 | 0 | 0 | 0 |
| 8M | 664 | 0 | 0 | 0 | 0 | 0 |
| 9M | 664 | 0 | 0 | 0 | 0 | 0 |
| 10M | 664 | 0 | 0 | 0 | 1 | 0 |
| 1F | 841 | 0 | 0 | 0 | 0 | 2 |
| 2F | 841 | 0 | 0 | 0 | 0 | 0 |
| 3F | 841 | 0 | 0 | 0 | 0 | 0 |

TABLE 3-continued

| Subject | Sample | Background | 0-3 hrs | 3-6 hrs | 6-9 hrs | 24 hrs |
|---------|--------|------------|---------|---------|---------|--------|
| 4F | 841 | 0 | 0 | 0 | 0 | 1 |
| 5F | 841 | 0 | 2 | 2 | 2 | 0 |
| 6F | 841 | 0 | 0 | 2 | 0 | 0 |
| 7M | 841 | 0 | 0 | 0 | 0 | 0 |
| 8M | 841 | 0 | 1 | 1 | 0 | 2 |
| 9M | 841 | 0 | 2 | 1 | 1 | 2 |
| 10M | 841 | 0 | 0 | 0 | 1 | 2 |

664 = placebo (1/10 responders)
495 = 100 mg/15.2 oz (3/10 responders)
841 = 200 mg/15.2 oz (7/10 responders)

There is a dose response from 100 to 200 mg PACS compared to placebo. Men did not respond to the Sample 495 juice, but they did respond to the Sample 841 juice. Women responded about the same for both those juices.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing a proanthocyanidin-containing beverage, the method comprising:
   (a) providing a mixture of cranberry leaves and water, wherein the leaves are provided in the mixture at about 0.5% to 20% w/w;
   (b) steeping the leaves in the water at 70° F. to 250° F. for about 20 minutes to extract proanthocyanidins thereby creating a proanthocyanidin-containing consumable solution;
   (c) separating the steeped leaves from the proanthocyanidin-containing consumable solution; and
   (d) combining the proanthocyanidin-containing consumable solution or a fraction derived therefrom with one or more additional components, to thereby produce a proanthocyanidin-containing beverage.

2. The method of claim 1, further comprising prior to step (a), harvesting cranberry leaves from cranberry plants, drying the leaves, and grinding the leaves to an average particle size of between about 0.25 mm and 1 mm.

3. The method of claim 1, further comprising prior to step (a) drying the leaves.

4. The method of claim 3, wherein the leaves are frozen prior to drying.

5. The method of claim 2, wherein the leaves are harvested after cranberries are harvested from the cranberry plants.

6. The method of claim 2, wherein the leaves are harvested in the spring before cranberry fruits are formed.

7. The method of claim 2, wherein the leaves are harvested in the fall.

8. The method of claim 1, further comprising clarifying the proanthocyanidin-containing consumable solution to produce a clarified proanthocyanidin-containing consumable solution.

9. The method of claim 1, further comprising concentrating the proanthocyanidin-containing consumable solution to at least 20% solids by weight.

10. The method of claim 1, further comprising heating the proanthocyanidin-containing consumable solution to at least or about 185° F. for at least 10 minutes.

11. The method of claim 1, further comprising spraying the proanthocyanidin-containing consumable solution onto a carrier, and then drying the carrier.

12. The method of claim 1, wherein all steps are performed in a continuous process.

13. The method of claim 12, wherein the continuous process further comprises grinding the cranberry leaves in the water.

14. The method of claim 12, wherein the continuous process further comprises stripping aroma from the cranberry leaves.

15. The method of claim 12, wherein separating comprises decanting the proanthocyanidin-containing consumable solution to remove cranberry leaves.

16. The method of claim 12, wherein separating comprises centrifuging the proanthocyanidin-containing consumable solution to remove cranberry leaves.

17. The method of claim 12, wherein the continuous process further comprises, after separating, evaporating the proanthocyanidin-containing consumable solution to a Brix content of about 40° to 60° Brix.

18. The method of claim 1, wherein one of the one or more additional components is selected from the group consisting of: water, a juice, a sweetener, a natural or artificial flavor, and a tisane.

19. The method of claim 1, wherein the leaves are provided in the mixture at about 1% to 20% w/w.

20. The method of claim 1, wherein the leaves are provided in the mixture at about 1% to 12% w/w.

21. The method of claim 1, wherein the leaves are provided in the mixture at about 5% to 15% w/w.

22. The method of claim 1, wherein the leaves are provided in the mixture at about 5% to 10% w/w.

23. The method of claim 1, wherein the leaves are provided at about 90% purity by weight.

24. The method of claim 1, wherein the leaves are provided at about 95% purity by weight.

25. The method of claim 1, wherein the leaves are provided at about 98% purity by weight.

26. The method of claim 1, wherein the leaves are provided at about 99% purity by weight.

27. The method of claim 1, wherein steeping the leaves comprises countercurrent extraction, kettle brewing, percolation, or any combination thereof.

28. The method of claim 1, the method comprising steeping the leaves in the water at 212° F.

29. A method of producing a proanthocyanidin-containing beverage, the method comprising:
   (a) providing a mixture of cranberry leaves and water, wherein the leaves are provided in the mixture at about 0.5% to 20% w/w;
   (b) steeping the leaves in the water at 70° F. to 250° F. for about 20 minutes to extract proanthocyanidins, thereby creating a proanthocyanidin-containing solution;
   (c) separating the steeped leaves from the proanthocyanidin-containing solution;
   (d) concentrating the proanthocyanidin-containing solution by filtration, thereby creating a concentrated solution; and
   (e) adding the concentrated solution to a water or juice, thereby producing a proanthocyanidin-containing beverage.

30. The method of claim 1, further comprising repeating step (b) at least once to extract more proanthocyanidins prior to step (c).

* * * * *